(12) United States Patent
Hebeisen et al.

(10) Patent No.: US 7,897,621 B2
(45) Date of Patent: Mar. 1, 2011

(54) 2-TRIFLUOROMETHYLNICOTINAMIDE DERIVATIVES AS HDL-CHOLESTEROL RAISING AGENTS

(75) Inventors: Paul Hebeisen, Basel (CH); Constantinos G. Panousis, Lyndhurst, NJ (US); Stephan Roever, Inzlingen (DE); Pius Waldmeier, Wegenstetten (CH); Matthew Wright, Basel (CH)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 12/404,364

(22) Filed: Mar. 16, 2009

(65) Prior Publication Data
US 2009/0247588 A1   Oct. 1, 2009

(30) Foreign Application Priority Data
Mar. 31, 2008 (EP) .................................. 08153792

(51) Int. Cl.
*A61K 31/44* (2006.01)
*C07D 213/62* (2006.01)
(52) U.S. Cl. ........................ 514/335; 514/346; 546/261; 546/298
(58) Field of Classification Search ................. 546/300, 546/298, 261; 514/345, 346
See application file for complete search history.

(56) References Cited
U.S. PATENT DOCUMENTS

| 7,229,999 | B2 | 6/2007 | Hebeisen et al. |
| 2006/0229326 | A1 | 10/2006 | Hebeisen et al. |
| 2007/0293509 | A1 | 12/2007 | Hebeisen et al. |
| 2008/0070931 | A1 | 3/2008 | Hebeisen et al. |
| 2008/0085905 | A1 | 4/2008 | Dietz et al. |
| 2008/0085906 | A1 | 4/2008 | Andjelkovic et al. |

FOREIGN PATENT DOCUMENTS

| WO | WO 2005/073192 | 8/2005 |
| WO | WO 2006/106054 | 10/2006 |
| WO | WO 2007/147746 | 12/2007 |
| WO | WO 2008/031734 | 3/2008 |
| WO | WO 2008/040651 | 4/2008 |
| WO | WO 2008/040649 | 10/2008 |

OTHER PUBLICATIONS

Andjelkovic et. al, Hcaplus 2008:441504, "Preparation of 3-pyridinecarboxamides and 2-pyrazinecarboxamides as HDL chloesterol raising agents.", Andjelkovic et. al., 102 e date Sep. 24, 2007.*
Patani et. al., "Bioisosterism: A Rational Approach in Drug Design", Patani et. al., Chem. Rev. 1996, 96, pp. 3147-3176.*

* cited by examiner

*Primary Examiner*—Janet L Andres
*Assistant Examiner*—Binta M Robinson
(74) *Attorney, Agent, or Firm*—George W. Johnston; Dennis P. Tramaloni; Brian C. Remy

(57) ABSTRACT

The present invention relates to compounds formula I:

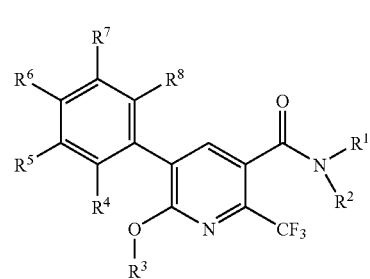

and pharmaceutically acceptable salts thereof, wherein $R^1$ to $R^8$ are as defined in the description and claims for use as HDL-cholesterol raising agents in the treatment and/or prophylaxis of diseases or disorders that can be treated with such agents such as dyslipidemia.

26 Claims, No Drawings

2-TRIFLUOROMETHYLNICOTINAMIDE DERIVATIVES AS HDL-CHOLESTEROL RAISING AGENTS

PRIORITY TO RELATED APPLICATION(S)

This application claims the benefit of European Patent Application No. 08153792.0, filed Mar. 31, 2008, which is hereby incorporated by reference in its entirety.

BACKGROUND OF THE INVENTION

The present invention relates to 2-trifluoromethylnicotinamide derivatives, their manufacture, pharmaceutical compositions containing them and their use as HDL-cholesterol raising agents. The compounds of the present invention are especially useful for the treatment of dyslipidemia.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are 3 different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (~10-12%). As a result, there is a significant unmet medical need for a well tolerated agent which can significantly elevate plasma HDL levels.

Thus, HDL-cholesterol raising agents can be useful as medicaments for the treatment and/or prophylaxis of atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, HDL-cholesterol raising agents may be used in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesteryl ester transfer protein (CETP) inhibitor, a cholesterol absorption inhibitor, a cholesterol synthesis inhibitor, a fibrate, niacin, preparations containing niacin or other HM74a agonists, an ion-exchange resin, an antioxidant, an ACAT inhibitor or a bile acid sequestrant.

Object of the present invention is therefore to provide compounds which are potent HDL-cholesterol raising agents. It has been found that compounds of formula I of the present invention are useful for the treatment and/or prophylaxis of diseases which can be treated with HDL-cholesterol raising agents, i.e. compounds of formula I are especially useful for the treatment and/or prevention of dyslipidemia. Object of the present invention is also to provide compounds which are, at therapeutically active concentrations, not interacting with the CB1-receptor. This is because CB1-receptor ligands would compromise the therapeutic utility of HDL-cholesterol raising agents as both agonists and antagonists of the CB1 receptor could lead to unacceptable CNS side effects. This requirement is of special importance for compounds of formula I as they share common structural elements with known CB1-receptor antagonists (WO 2006/106054) and mixed CB1 receptor antagonists/HDL cholesterol raising agents (WO 2008/040651).

SUMMARY OF THE INVENTION

The present invention relates to the compounds of formula I:

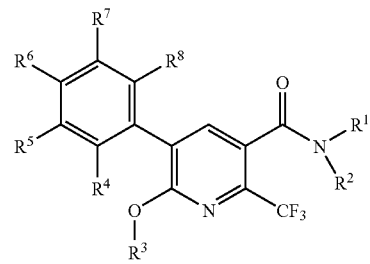

and pharmaceutically acceptable salts thereof, wherein:
$R^1$ is selected from the group consisting of:
  (1) lower hydroxyalkyl,
  (2) cycloalkyl which is unsubstituted or substituted by hydroxy or lower hydroxyalkyl, and
  (3) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
  (1) lower alkoxyalkyl,
  (2) lower halogenalkyl, and
  (3) lower heteroarylalkyl, wherein the heteroaryl group is unsubstituted or substituted once or twice by lower alkyl;
$R^4$ and $R^8$ are hydrogen; and
$R^5$, $R^6$ and $R^7$ independently from each other are selected from the group consisting of:
  (1) hydrogen,
  (2) lower alkyl,
  (3) halogen,
  (4) lower halogenalkyl,
  (5) lower halogenalkoxy,
  (6) lower alkylsulfonylamino, and
  (7) cyano.

The compounds of formula I are HDL-cholesterol raising agents and are useful in the treatment and/or prophylaxis of diseases or disorders that can be treated with such agents such as dyslipidemia.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven carbon atom(s). In preferred embodiments a "lower" group has one to four carbon atom(s).

The term "alkyl", alone or in combination with other groups, refers to a branched or straight-chain monovalent saturated aliphatic hydrocarbon radical of one to twenty carbon atoms. In preferred embodiments the akyl has one to sixteen carbon atoms, and more preferably one to ten carbon atoms.

The term "lower alkyl" or "$C_{1-7}$-alkyl", alone or in combination with other groups, refers to a branched or straight-chain monovalent alkyl radical of one to seven carbon atoms. In preferred embodiments the lower akyl has one to four carbon atoms. This term is exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "alkoxy" refers to the group R'—O—, wherein R' is alkyl. The term "lower alkoxy" or "$C_{1-7}$-alkoxy" refers to the group R'—O—, wherein R' is lower alkyl. Examples of lower alkoxy groups include methoxy, ethoxy, propoxy, isopropoxy, butoxy, isobutoxy and hexyloxy, with methoxy being especially preferred.

The term "lower alkoxyalkyl" or "$C_{1-7}$-alkoxy-$C_{1-7}$-alkyl" refers to a lower alkyl group as defined above which is mono- or multiply substituted with a lower alkoxy group as defined above. Examples of lower alkoxyalkyl groups include —$CH_2$—O—$CH_3$, —$CH_2$—$CH_2$—O—$CH_3$, —$CH_2$—O—$CH_2$—$CH_3$ and the groups specifically exemplified herein. Most preferably, lower alkoxyalkyl is methoxyethyl.

The term "lower hydroxyalkyl" or "hydroxy-$C_{1-7}$-alkyl" refers to a lower alkyl group as defined above wherein at least one of the hydrogen atoms of the lower alkyl group is replaced by a hydroxy group. Preferred are $C_{3-7}$-hydroxyalkyl groups. Examples of lower hydroxyalkyl groups include 2-hydroxybutyl, 3-hydroxy-2,2-dimethylpropyl and the groups specifically exemplified herein.

The term "halogen" refers to fluoro, chloro, bromo and iodo. Preferred "halogen" groups are fluoro or chloro.

Unless otherwise indicated, the term "hydrogen" or "hydro" refers to the moiety of a hydrogen atom (—H) and not $H_2$.

The term "lower halogenalkyl" or "halogen-$C_{1-7}$-alkyl" refers to a lower alkyl group which is mono- or multiply substituted with halogen. In preferred embodiments the halogen of a lower halogenalkyl is fluoro or chloro, most preferably fluoro. Examples of lower halogenalkyl groups include —$CF_3$, —$CHF_2$, —$CH_2Cl$, —$CH_2CF_3$, —$CH(CF_3)_2$, —$CF_2$—$CF_3$ and the groups specifically exemplified herein.

The term "lower halogenalkoxy" or "halogen-$C_{1-7}$-alkoxy" refers to a lower alkoxy group as defined above wherein at least one of the hydrogen atoms of the lower alkoxy group is replaced by a halogen atom. In preferred embodiments, the halogen of a lower halogenalkoxy group is fluoro or chloro, and most preferably fluoro. Among the preferred lower halogenalkoxy groups are trifluoromethoxy, difluoromethoxy, fluormethoxy and chloromethoxy, with trifluoromethoxy being especially preferred.

The term "cycloalkyl" or "$C_{3-7}$-cycloalkyl" refers to a monovalent carbocyclic radical of three to seven carbon atoms. In preferred embodiments the cycloalkyl has three to five carbon atoms. This term is exemplified by radicals such as cyclopropyl, cyclobutyl, cyclopentyl, cyclohexyl and cycloheptyl, with cyclopropyl being especially preferred.

The term "lower cycloalkylalkyl" or "$C_{3-7}$-cycloalkyl-$C_{1-7}$-alkyl" refers to a lower alkyl group as defined above which is mono- or multiply substituted with a cycloalkyl group as defined above. Examples of lower cycloalkylalkyl groups include —$CH_2$-cyclopropyl, —$CH_2$—$CH_2$—cyclopropyl, —$CH_2$-cyclopentyl and the groups specifically exemplified herein.

The term "heteroaryl" refers to an aromatic 5- or 6-membered ring which comprises one, two or three heteroatoms independently selected from the group consisting of nitrogen, oxygen and sulphur. Examples of heteroaryl groups include furyl, pyridyl, pyrazinyl, pyrimidinyl, pyridazinyl, thienyl, isoxazolyl, thiazolyl, isothiazolyl, oxazolyl, imidazolyl, pyrazolyl, triazolyl, oxadiazolyl, oxatriazolyl, tetrazolyl, pentazolyl, and pyrrolyl. The heteroaryl group can optionally be mono- or disubstituted by lower alkyl. The term "heteroaryl" also includes bicyclic aromatic moieties having 9 to 10 ring atoms with 1 to 3 heteroatoms such as benzofuranyl, benzothiazolyl, indolyl, benzoxazolyl, quinolinyl, isoquinolinyl, benzimidazolyl, benzisoxazolyl, and benzothienyl. Preferred heteroaryl groups are isoxazolyl, pyridyl, pyrimidinyl, imidazolyl, triazolyl, and thiazolyl which groups can optionally be mono- or disubstituted by lower alkyl. Especially preferred are 3-methylisoxazolyl, 5-methylisoxazolyl, pyridyl, 3-methylpyridyl, pyrimidinyl, 1-methylimidazolyl, 2-methyl[1,2,4]triazolyl and 4-methylthiazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "lower alkylsulfonyl" or "$C_{1-7}$-alkylsulfonyl" refers to the group R'—$SO_2$—, wherein R' is lower alkyl. Examples of lower alkylsulfonyl groups include methanesulfonyl and ethanesulfonyl.

The term "lower alkylsulfonylamino" or "$C_{1-7}$-alkylsulfonylamino" refers to the group R'—$SO_2$—NH—, wherein R' is lower alkyl. A preferred lower alkylsulfonylamino group is methanesulfonylamino.

The term "pharmaceutically acceptable salts" embraces salts of the compounds of formula I with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, salicylic acid, p-toluenesulphonic acid and the like, which are non toxic to living organisms. Preferred salts with acids are formates, maleates, citrates, hydrochlorides, hydrobromides and methanesulfonic acid salts, with hydrochlorides being especially preferred.

Unless otherwise indicated, in reference to a particular group or moleucle, the term "substituted" refers to the fact that at least one of the hydrogen atoms of that group or molecule is replaced by some other substituent.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt of any such compound).

In detail, the present invention relates to the compounds of formula I:

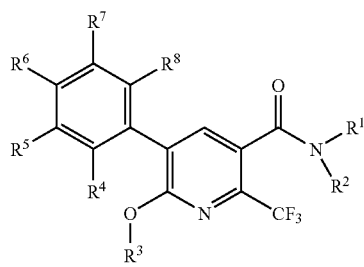

I or pharmaceutically acceptable salts thereof, wherein
R' is selected from the group consisting of:
  (1) lower hydroxyalkyl,
  (2) cycloalkyl which is unsubstituted or substituted by hydroxy or lower hydroxyalkyl, and
  (3) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
  (1) lower alkoxyalkyl,
  (2) lower halogenalkyl, and
  (3) lower heteroarylalkyl, wherein the heteroaryl group is unsubstituted or substituted once or twice by lower alkyl;
$R^4$ and $R^8$ are hydrogen; and
$R^5$, $R^6$ and $R^7$ independently from each other are selected from the group consisting of:
  (1) hydrogen,
  (2) lower alkyl,
  (3) halogen,
  (4) lower halogenalkyl,
  (5) lower halogenalkoxy,
  (6) lower alkylsulfonylamino, and
  (7) cyano.

Preferred compounds of formula I according to the invention are those, wherein $R^3$ is lower halogenalkyl or lower heteroarylalkyl, wherein the heteroaryl group is unsubstituted or mono- or di-substituted by lower alkyl.

More preferred are compounds of formula I, wherein $R^3$ is lower halogenalkyl, with those compounds of formula I, wherein $R^3$ is 2,2,2-trifluoroethyl, being especially preferred.

Also preferred are compounds of formula I, wherein $R^3$ is lower heteroarylalkyl, wherein the heteroaryl group is unsubstituted or mono- or di-substituted by lower alkyl, with those compounds of formula I, wherein $R^3$ is pyridylmethyl, being especially preferred.

Furthermore, compounds of formula I according to the invention are preferred, wherein $R^1$ is cycloalkyl substituted by hydroxy, with those compounds, wherein $R^1$ is cyclohexyl substituted by hydroxy, being especially preferred.

Another group of preferred compounds of formula I according to the present invention are those, wherein $R^1$ is —$CH_2$—$CR^9R^{10}$-cycloalkyl and wherein $R^9$ is methyl and $R^{10}$ is hydroxy, with those compounds of formula I, wherein $R^1$ is —$CH_2$—$CR^9R^{10}$-cyclopropyl and wherein $R^9$ is methyl and $R^{10}$ is hydroxy, being more preferred.

A further group of preferred compounds of formula I according to the present invention are those, wherein $R^1$ is lower hydroxyalkyl, with those compounds of formula I, wherein $R^1$ is 1-hydroxymethyl-3-methylbutyl, being especially preferred.

Also preferred are compounds of formula I according to the invention, wherein at least one of $R^5$, $R^6$ and $R^7$ is selected from the group consisting of lower alkyl, halogen, lower halogenalkyl, lower halogenalkoxy, lower alkylsulfonylamino and cyano.

Furthermore, compounds of formula I are preferred, wherein at least one of $R^5$, $R^6$ and $R^7$ is selected from halogen or lower alkylsulfonylamino, with those compounds of formula I, wherein $R^6$ is halogen or lower alkylsulfonylamino and $R^5$ and $R^7$ are hydrogen, being more preferred. Especially preferred are compounds of formula I, wherein $R^6$ is chloro.

Also preferred are compounds of formula I according to the invention, wherein $R^5$ and $R^6$ are halogen and $R^7$ is hydrogen. Especially preferred are compounds of formula I, wherein $R^5$ and $R^6$ are chloro.

Preferred compounds of formula I according to the invention are selected from the group consisting of:

5-(4-chloro-phenyl)-N-(2-cyclopropyl-2-hydroxy-propyl)-6-(2,2,2-trifluoro-ethoxy)-2-trifluoromethyl-nicotinamide, N-(2-cyclopropyl-2-hydroxy-propyl)-5-(3,4-dichloro-phenyl)-6-(2,2,2-trifluoro-ethoxy)-2-trifluoromethyl-nicotinamide, N-((R)-2-cyclopropyl-2-hydroxy-propyl)-5-(3,4-dichloro-phenyl)-6-(2,2,2-trifluoro-ethoxy)-2-trifluoromethyl-nicotinamide N-((S)-2-cyclopropyl-2-hydroxy-propyl)-5-(3,4-dichloro-phenyl)-6-(2,2,2-trifluoro-ethoxy)-2-trifluoromethyl-nicotinamide 5-(3-chloro-phenyl)-N-(2-cyclopropyl-2-hydroxy-propyl)-6-(2,2,2-trifluoro-ethoxy)-2-trifluoromethyl-nicotinamide, 5-(4-chloro-phenyl)-N-((1R,2R)-2-hydroxy-cyclohexyl)-6-(2,2,2-trifluoro-ethoxy)-2-trifluoromethyl-nicotinamide, 5-(4-Chloro-phenyl)-N-((1R,2S)-2-hydroxy-cyclohexyl)-6-(2,2,2-trifluoro-ethoxy)-2-trifluoromethyl-nicotinamide, 5-(4-Chloro-phenyl)-N-((1S,2R)-2-hydroxy-cyclohexyl)-6-(2,2,2-trifluoro-ethoxy)-2-trifluoromethyl-nicotinamide, 5-(4-chloro-phenyl)-N-((1S,2S)-2-hydroxy-cyclohexyl)-6-(2,2,2-trifluoro-ethoxy)-2-trifluoromethyl-nicotinamide, N-(1-hydroxymethyl-3-methyl-butyl)-5-(4-methanesulfonylamino-phenyl)-6-(pyridin-2-ylmethoxy)-2-trifluoromethyl-nicotinamide, N-((1R,2R)-2-hydroxy-cyclohexyl)-5-(4-methanesulfonylamino-phenyl)-6-(2,2,2-trifluoro-ethoxy)-2-trifluoromethyl-nicotinamide, 5-(3,4-dichloro-phenyl)-N-((1R,2R)-2-hydroxy-cyclohexyl)-6-(pyridin-2-ylmethoxy)-2-trifluoromethyl-nicotinamide, and all pharmaceutically acceptable salts thereof.

Especially preferred is a compound of formula I of the present invention that is 5-(4-Chloro-phenyl)-N-((1R,2S)-2-hydroxy-cyclohexyl)-6-(2,2,2-trifluoro-ethoxy)-2-trifluoromethyl-nicotinamide.

The compounds of formula I of the invention can be prepared by a process, which process comprises:

coupling a compound of formula

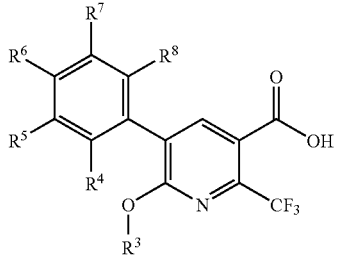

II

wherein $R^3$ to $R^8$ are as defined herein before, with an amine of the formula

H—NR$^1$R$^2$　　　III wherein $R^1$ and $R^2$ are as defined herein before, with the help of an coupling agent under basic conditions, and, if desired, converting the resulting compound of formula I into a pharmaceutically acceptable salt thereof.

Coupling agents for the reaction of compounds of formula II with amines of formula III are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU). Preferred coupling agent is TBTU. Suitable bases include triethylamine, diisopropylethylamine and, preferably, Hünig's base.

Alternatively the amide coupling can be affected by forming the corresponding acid chloride IIa from II which is then reacted with an amine of formula III to give a compound of formula I, i.e. the compounds of formula I of the invention can be prepared by a process, which process comprises:

coupling a compound of formula

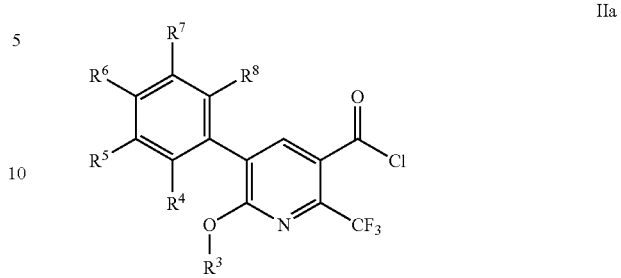

IIa

wherein $R^3$ to $R^8$ are as defined herein before, with an amine of the formula

H—NR$^1$R$^2$　　　III wherein $R^1$ and $R^2$ are as defined herein before, and, if desired, converting the resulting compound of formula I into a pharmaceutically acceptable salt thereof.

Alternatively, the compounds can be prepared by a process, which process comprises: coupling a compound of formula

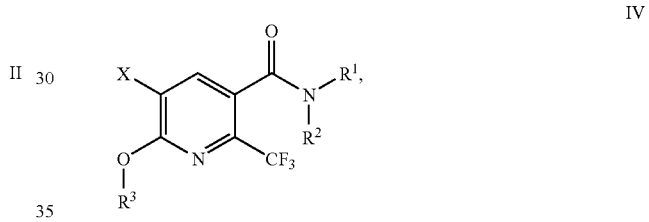

IV wherein X is halogen and $R^1$, $R^2$ and $R^3$ are as defined herein before, with an aryl metal species of the formula

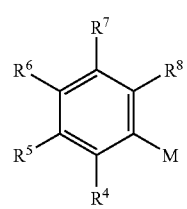

V wherein $R^4$ to $R^8$ are as defined herein before and M means boronic acid or a boronic acid ester, in the presence of a Pd catalyst under basic conditions, and, if desired, converting the resulting compound of formula I into a pharmaceutically acceptable salt thereof.

The aryl metal species is preferably an aryl boronic acid or arylboronic acid ester. The palladium catalyst is preferably a palladium(II)chloride-dppf complex which is used in the presence of a base, preferably sodium carbonate. X is halogen, more preferably X is bromo or iodo.

Thus, the compounds of formula I can be manufactured by the methods given in the examples and according to the synthesis as described in scheme 1 below. Starting materials are either commercially available or can be prepared by methods analogous to the methods given below or in the examples or by methods known in the art.

Scheme 1

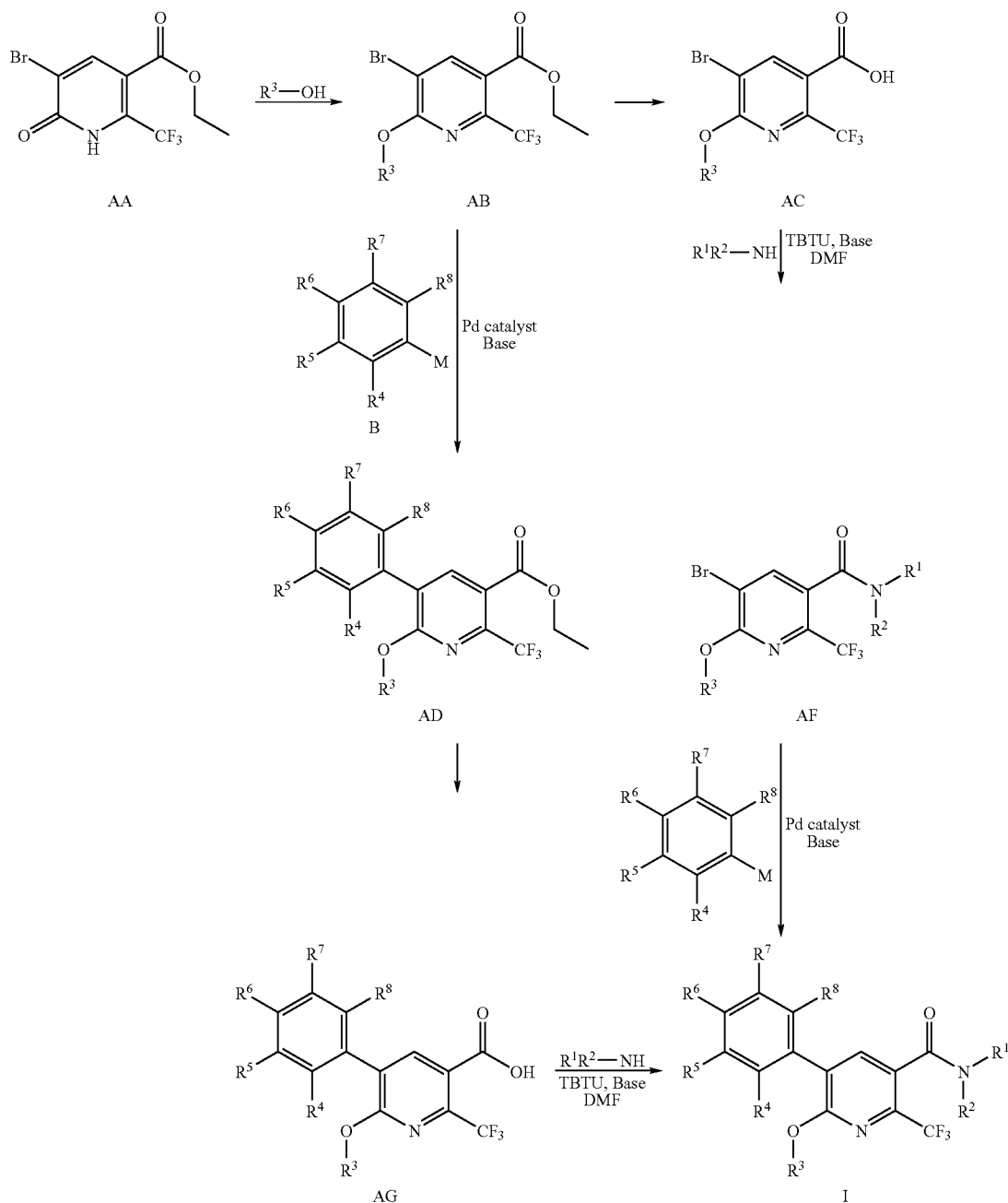

Following the procedure according to scheme 1, compound AA (5-bromo-1,6-dihydro-6-oxo-2-(trifluoromethyl)-3-pyridinecarboxylic acid ethyl ester, CAS Registry No. 862111-61-3) can be used as starting material. AA can be prepared by a two step sequence from ethyl-4,4,4,-trifluoro-acetatoacetate and acrylamide following literature procedures (WO 2005/073192).

Compound AB can be prepared from AA by Mitsonobu reaction with a suitably substituted primary or secondary alcohol $R^3$—OH in the presence of triphenylphosphine and an activating agent like diethylazo dicarboxylate, in a inert solvent, for example THF, at temperatures from 0° C. to reflux temperature of the solvent, preferably at 50° C.

Compound AC can then be obtained by saponification of compound AB by methods known in the art, for example by saponification with an alkalimetal hydroxide, for example lithium hydroxide, in a suitable solvent, for example a mixture of THF and water.

In the following step compounds of formula AF are obtained from compound AC and the corresponding amine of formula $R^1R^2NH$ (III) by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformation. A convenient method is to use for example TBTU and a base, for example Hünig's base (N-ethyldiisopropylamine) in an inert solvent such as for example dimethylformamide at room temperature. Alternatively a corresponding acid chloride can be prepared from the acid AC by methods well known in the art which is then reacted with an amine of formula III, optionally in the presence of a base, to give a compound of formula AF.

Compounds of formula I can also be prepared by coupling a suitably substituted aryl metal species of formula B, preferably a arylboronic acid or arylboronic acid ester, with AF in the presence of a suitable catalyst, preferably a palladium catalyst and more preferably palladium(II)acetate/triphenylphosphine mixtures or palladium(II)chloride-dppf (1,1'-bis(diphenylphosphino)ferrocene) complexes and a base, preferably triethylamine or sodium carbonate in an inert solvent such as dimethylformamide or toluene.

The saponification, amide coupling and Suzuki reaction as described in scheme 1 need not necessarily be run in this sequence. An alternative viable sequence would be Suzuki reaction (AB to AD) followed by saponification (AD to AG) and finally amide coupling to arrive at compounds of formula I.

The literature procedure to prepare the starting material AA as described above is of low yield, suffers from polymerization side products in the first step and is generally unsuitable for upscaling (cf. Brown et al. Organic Process Research & Development (1997), 1(5), 370-378). Advantageously, compound AA can be prepared from acryloylchloride and an 3-amino-4,4,4-trifluoro-2-butenoic acid ester followed by a bromination, dehydrobromination, bromination sequence. This alternative procedure (scheme 2) is described in the experimental part and has the advantage of higher yield and avoiding polymerization by-products in the first step.

Scheme 2

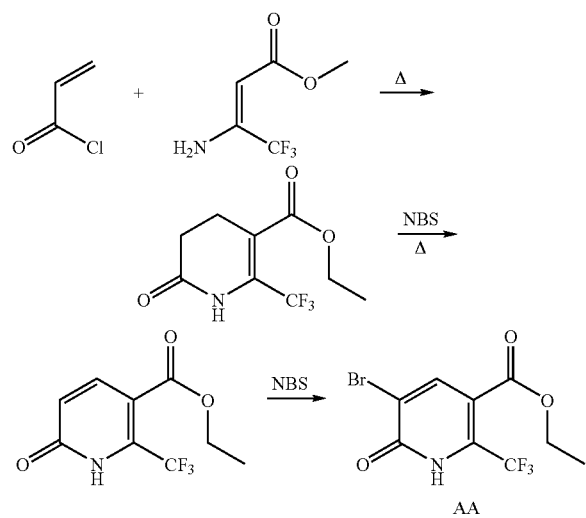

As described above, the compounds of formula I of the present invention can be used as medicaments for the treatment and/or prophylaxis of diseases which can be treated with HDL-cholesterol raising agents. "Diseases which can be treated with HDL-cholesterol raising agents" means such diseases as atherosclerosis, peripheral vascular disease, dyslipidemia, hyper-betalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. Preferably, such diseases are atherosclerosis, peripheral vascular disease and dyslipidemia. Most preferably, the disease is dyslipidemia.

The invention therefore also relates to a pharmaceutical composition comprising a compound as defined above and a pharmaceutically acceptable carrier and/or adjuvant which is useful for the treatment and/or prophylaxis of diseases which can be treated with HDL-cholesterol raising agents.

Thus, the invention relates to a pharmaceutical composition as defined above for the treatment and/or prophylaxis of atherosclerosis, peripheral vascular disease, dyslipidemia, hyperbetalipoproteinemia, hypoalphalipoproteinemia, hypercholesterolemia, hyper-triglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which can be treated with HDL-cholesterol raising agents, which method comprises administering a therapeutically effective amount of a compound of formula I to a patient in need thereof.

In addition, the invention relates to the use of compounds of formula I as defined above for the preparation of a medicament for the treatment and/or prophylaxis of diseases that can be treated with HDL raising agents.

In addition, the compounds of formula I are useful in combination or association with another compound, said compound being selected from the group consisting of an HMG-CoA reductase inhibitor, an microsomal triglyceride transfer protein (MTP)/ApoB secretion inhibitor, a PPAR activator, a cholesteryl ester transfer protein (CETP) inhibitor, a bile acid reuptake inhibitor, a cholesterol absorption inhibitor, a cholesterol synthesis inhibitor, a fibrate, niacin, a preparation containing niacin or other HM74a agonists, an ion-exchange resin, an antioxidant, an ACAT inhibitor or a bile acid sequestrant.

The compounds of formula I and/or their pharmaceutically acceptable salts can be used in the form of pharmaceutical compositions for enteral, parenteral or topical administration. They can be administered, for example, perorally, e.g. in the form of tablets, coated tablets, dragées, hard and soft gelatine capsules, solutions, emulsions or suspensions, orally, e.g. in the form of buccal cavities, rectally, e.g. in the form of suppositories, parenterally, e.g. in the form of injection solutions or infusion solutions for intramuscular, intravenous or subcutaneous injection, or topically, e.g. in the form of ointments, creams or oils. Oral administration is preferred.

The production of the pharmaceutical compositions can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The therapeutically effective amount or dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 100 mg, especially about 1 to 50 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 1 to 100 mg, preferably 5 to 50 mg, of a compound of formula I.

The following tests were carried out in order to determine the activity of the compounds of formula I and their valuable pharmacological properties.

Cholesterol Efflux Assay

The ability of compounds of the invention to stimulate cholesterol efflux is determined in replicate cultures of THP-1 cells in 96-well microplates. Cells are plated at an initial density of 150,000 cells/well and differentiated to macrophages with the addition of PMA (100 ng/ml) for 72 hrs in 10% fetal bovine serum, 3 µl/L of b-mercaptoethanol, RPMI-1640 medium. Cells are washed once with RPMI-1640 and loaded with RPMI-1640 medium containing 2% FCS, 50 µg/ml acetylated LDL, and 10 µCi/ml [$^3$H]cholesterol for 48 hours at 37° C. After loading the cells are washed once with RPMI-1640 and incubated with the compound of interest from DMSO solutions for an additional 24 hrs in RPMI-1640 medium containing 1 mg/ml fatty acid free-bovine serum albumin (BSA). Upon incubation cells are washed once, and cholesterol efflux is induced by the addition of 10 µg/ml Apolipoprotein AI in RPMI-1640 containing 1 mg/ml BSA and in the presence of the compound for an additional 6 hrs. Following incubation radioactivity is determined in the supernatants and cholesterol efflux is expressed as the percent stimulation over replicate cultures treated only with DMSO. Sigmoidal curves were fitted using the XLfit3 program (ID Business Solutions Ltd. UK) and $EC_{50}$ values were determined.

The compounds of the present invention exhibit $EC_{50}$ values in a range of 0.1 µM to 3.0 µM in the cholesterol efflux assay. Preferably, the compounds of the present invention have $EC_{50}$ values in a range of 0.1 µM to 1.5 µM. Representative compounds with their corresponding $EC_{50}$ values in the cholesterol efflux assay are shown below:

| Example | $EC_{50}$ [µM] |
| --- | --- |
| 1 | 0.45 |
| 2 | 1.07 |
| 2A | 1.63 |
| 2B | 1.40 |
| 3 | 0.48 |
| 4 | 0.39 |
| 4A | — |
| 4B | 1.20 |
| 4C | 2.50 |
| 5 | 0.89 |
| 6 | 0.56 |
| 7 | 0.64 |

Affinity Towards Cannabinoid CB1 Receptor

The affinity of the compounds of formula I of the present invention towards cannabinoid CB1 receptors was determined as described in WO 2006/106054, page 36. Surprisingly, the compounds of the present invention show only poor affinity for the CB1 receptor compared to the compounds of WO 2006/106054.

The compounds of the present invention exhibit $IC_{50}$ values in a range of 1 µM to >30 µM in the CB1-receptor binding assay. Preferably, the compounds of the present invention have $IC_{50}$ values in a range of >10 µM to >30 µM. Representative compounds with their corresponding $IC_{50}$ values in the CB1-receptor binding assay are shown below:

| Example | $IC_{50}$ [µM] |
| --- | --- |
| 1 | ~10 |
| 2 | >10 |
| 2A | >10 |
| 2B | >10 |
| 3 | >10 |
| 4 | 5.6 |
| 4A | — |
| 4B | >10 |
| 4C | >10 |
| 5 | ~10 |
| 6 | >10 |
| 7 | >10 |

Further demonstration of biological activities of the compounds of the present invention may be accomplished through the following in vivo assays that are well known in the art.

Effects on Plasma Lipid Levels in Lean, Chow Fed Rats

Effects of compounds of compounds of formula I on plasma lipid levels were determined in lean, chow-fed Sprague-Dawley rats with compounds administered by p.o. gavage. After one week of acclimation, blood samples were collected from 4 hour-fasted animals for plasma lipid determination. Animals were then assigned to treatment groups based on HDL-cholesterol levels. Compounds of formula I were administered by gavage, once daily for five days. Control animals received vehicle alone. Blood was collected on day five from 4 hour-fasted rats, 2 hours after a final treatment, for plasma lipid analysis. Total cholesterol, HDL-cholesterol, and triglycerides were determined by measuring total cholesterol, HDL-cholesterol, and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Obese, High Fat Diet Fed Rats

Efficacy of compounds in modulating plasma lipid levels was determined also in obese male Sprague Dawley rats after 28-29 days administration of compounds. Male Sprague-Dawley rats of 10 weeks of age were fed a high fat diet during 3 weeks. Obese rats were distributed in groups according to homogeneous BW and FI evaluated a week before the start of the treatment. Treatment was administered as food-Admix. On day 29, blood was taken in the morning under slight anesthesia (retro-orbital method) in post-prandial conditions i.e. 4 h after food was removed. Plasma was separated from blood by low speed centrifugation and selected organs were taken (e.g liver, fat). Total cholesterol, HDL-cholesterol, and triglycerides were determined by measuring total cholesterol, HDL-cholesterol, LDL-cholesterol and triglyceride using colorimetric enzymatic assays (Roche Diagnostic GmbH, Mannheim, Germany). HDL-C was also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Hamsters

Efficacy of compounds in modulating plasma lipid levels was determined in hamsters after 5 days of daily administration of compounds. Male hamsters of 6-8 weeks of age were used in the studies. After one week of acclimation, blood samples were collected from 4 hour-fasted animals for plasma lipid determination. Animals were then assigned to treatment groups based on HDL-cholesterol levels. Compounds were administered by gavage, once daily for five days. Control animals received vehicle alone. Blood was collected on day five from 4 hour-fasted hamsters, 2 hours after a final treatment, for plasma lipid analysis. Total cholesterol, HDL-cholesterol, LDL-cholesterol, and triglycerides were determined using calorimetric enzymatic assays (Roche Diagnostic GmbH, Mannheim, Germany). HDL-cholesterol, LDL-cholesterol, and VLDL-cholesterol levels were also quantified using size exclusion chromatography on superpose-6 column using a SMART system (Pharmacia). Lipoprotein distribution was calculated assuming a Gaussian distribution for each peak, using a nonlinear, least-squares curve-fitting procedure to calculate the area under the curve. Compound concentration was also determined in plasma.

Effects on Plasma Lipid Levels in Cholesterol/Fat Fed Hamsters

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride changes.

EXAMPLES

The following are a list of abbreviations and/or acronyms with their corresponding definitions used in the following examples: TBTU refers to O-benzotriazol-1-yl-N,N,N',N'-tetramethyluronium tetrafluoroborate; DMF refers to dimethylformamide; RT refers to room temperature; THF refers to tetrahydrofuran; TBME refers to methyl tert-butyl ether; and MS refers to mass spectrometry.

Example 1

Preparation of 5-(4-chloro-phenyl)-N-(2-cyclopropyl-2-hydroxy-propyl)-6-(2,2,2-trifluoro-ethoxy)-2-trifluoromethyl-nicotinamide a) 5-Bromo-6-(2,2,2-trifluoro-ethoxy)-2-trifluoromethyl-nicotinic acid ethyl ester 5-Bromo-1,6-dihydro-6-oxo-2-(trifluoromethyl)-3-pyridinecarboxylic acid ethyl ester (CAS Registry No. 862111-61-3) (5.0 g, 16 mmol) was dissolved in tetrahydrofuran (80 mL). To the solution were added trifluoroethanol (1.37 mL, 19 mmol), triphenylphosphine (5.0 g, 19 mmol) and diethyl azodicarboxylate (3.7 mL, 19 mmol) at 0° C. The mixture was stirred for 30 min at 0° C. and for 6 h at room temperature. The solvent was removed in vacuo and the residue dissolved in dichloromethane and washed with water. Organic phases were pooled, dried with $MgSO_4$ and concentrated in vacuo. The residue was purified by chromatography on silica gel with dichloromethane:heptane 1:2 to yield the product as white solid, MS (ISP) 397 $(M+H)^+$.

b) 5-Bromo-6-(2,2,2-trifluoro-ethoxy)-2-trifluoromethyl-nicotinic acid

5-Bromo-6-(2,2,2-trifluoro-ethoxy)-2-trifluoromethyl-nicotinic acid ethyl ester (4.0 g, 10 mmol) was dissolved in a mixture of tetrahydrofuran (70 mL) and water (25 mL). Lithiumhydroxid monohydrate (1.26 g, 30 mmol) was added and the mixture was stirred and heated at reflux-temperature for 3 h. After cooling to room temperature the mixture was acidified with hydrochloric acid (1N) to pH 4. The product precipitated and was after filtration dried and isolated as a white solid (quant.); MS (ISP) 365.8, 367.8 (M–H).

c) 5-Bromo-N-(2-cyclopropyl-2-hydroxy-propyl)-6-(2,2,2-trifluoro-ethoxy)-2-trifluoromethyl-nicotinamide 5-Bromo-6-(2,2,2-trifluoro-ethoxy)-2-trifluoromethyl-nicotinic acid (1.1 g, 3.0 mmol) was dissolved in DMF (25 mL). To the solution was added TBTU (1.06 g, 3.3 mmol), N,N-diisopropylethyl amine (2.54 mL, 15 mmol) and α-(aminomethyl)-α-methyl-cyclopropanemethanol (0.38 g, 3.3 mmol). The reaction mixture was stirred for 16 h at room temperature. The solvent was evaporated in vacuo and the residue dissolved in ethyl acetate (20 mL), washed with sodium hydroxide solution (0.5 N) and brine. Organic phases were pooled, dried with MgSO4 and concentrated in vacuo.

The residue was purified by flash chromatography (SiO$_2$, heptane/ethyl acetate) to give the title compound (0.38 g) as a light yellow solid, MS (ISP) 462.9, 464.9 (M−H)$^+$.

d) 5-(4-Chloro-phenyl)-N-(2-cyclopropyl-2-hydroxy-propyl)-6-(2,2,2-trifluoro-ethoxy)-2-trifluoromethyl-nicotinamide 5-Bromo-N-(2-cyclopropyl-2-hydroxy-propyl)-6-(2,2,2-trifluoro-ethoxy)-2-trifluoromethyl-nicotinamide (0.09 g, 0.19 mmol) was dissolved in toluene (4 mL) and dimethylformamide (0.3 mL). To this solution was added with stirring [1,1'-bis(diphenylphosphino)ferrocene]dichloropalladium (II) CH$_2$Cl$_2$ (8 mg, 0.010 mmol), 4-chlorophenylboronic acid (32 mg, 0.20 mmol) and sodium carbonate solution (2M, 0.20 mL). This mixture was heated to 90° C. for 15 h and cooled to room temperature. Water (10 mL) was added, the phases were separated and the water mixture was extracted with ethylacetate. Organic phases were pooled, dried with MgSO4 and the volatiles removed in vacuo. The residue was purified by flash chromatography (SiO$_2$, dichloromethane/ethyl acetate) to give the title compound (53 mg) as a brown gum; MS (ISP) 497.2 (M)$^+$.

Example 2

Preparation of N-(2-cyclopropyl-2-hydroxy-propyl)-5-(3,4-dichloro-phenyl)-6-(2,2,2-trifluoro-ethoxy)-2-trifluoromethyl-nicotinamide The title compound was synthesized in analogy to Example 1d, using 5-bromo-N-(2-cyclopropyl-2-hydroxy-propyl)-6-(2,2,2-trifluoro-ethoxy)-2-trifluoromethyl-nicotinamide and 3,4-dichlorophenylboronic acid as starting materials, MS (ISP) 531.0, 533.0 (M)$^+$.

Example 2A

Preparation of N-((R)-2-cyclopropyl-2-hydroxy-propyl)-5-(3,4-dichloro-phenyl)-6-(2,2,2-trifluoro-ethoxy)-2-trifluoromethyl-nicotinamide a) 5-Bromo-N-((R)-2-cyclopropyl-2-hydroxy-propyl)-6-(2,2,2-trifluoro-ethoxy)-2-trifluoromethyl-nicotinamide The title compound was synthesized in analogy to Example 1c, using 5-bromo-6-(2,2,2-trifluoro-ethoxy)-2-trifluoromethyl-nicotinic acid and (R)-α-(aminomethyl)-α-methyl-cyclopropanemethanol as starting materials, MS (ISP) 462.9, 464.9 (M−H).

b) N-((R)-2-Cyclopropyl-2-hydroxy-propyl)-5-(3,4-dichloro-phenyl)-6-(2,2,2-trifluoro-ethoxy)-2-trifluoromethyl-nicotinamide The title compound was synthesized in analogy to Example 1d, using 5-bromo-N-((R)-2-cyclopropyl-2-hydroxy-propyl)-6-(2,2,2-trifluoro-ethoxy)-2-trifluoromethyl-nicotinamide and 3,4-dichlorophenylboronic acid as starting materials, MS (ISP) 531.0 (M+H)$^+$.

Example 2B

Preparation of N-((S)-2-cyclopropyl-2-hydroxy-propyl)-5-(3,4-dichloro-phenyl)-6-(2,2,2-trifluoro-ethoxy)-2-trifluoromethyl-nicotinamide a) 5-Bromo-N-((S)-2-cyclopropyl-2-hydroxy-propyl)-6-(2,2,2-trifluoro-ethoxy)-2-trifluoromethyl-nicotinamide The title compound was synthesized in analogy to Example 1c, using 5-bromo-6-(2,2,2-trifluoro-ethoxy)-2-trifluoromethyl-nicotinic acid and (S)-α-(aminomethyl)-α-methyl-cyclopropanemethanol as starting materials, MS (ISP) 465.0, 467.1 (M+H)$^+$.

b) N-((S)-2-Cyclopropyl-2-hydroxy-propyl)-5-(3,4-dichloro-phenyl)-6-(2,2,2-trifluoro-ethoxy)-2-trifluoromethyl-nicotinamide The title compound was synthesized in analogy to Example 1d, using 5-bromo-N—((S)-2-cyclopropyl-2-hydroxy-propyl)-6-(2,2,2-trifluoro-ethoxy)-2-trifluoromethyl-nicotinamide and 3,4-dichlorophenylboronic acid as starting materials, MS (ISP) 531.1 (M+H)$^+$.

Example 3

Preparation of 5-(3-chloro-phenyl)-N-(2-cyclopropyl-2-hydroxy-propyl)-6-(2,2,2-trifluoro-ethoxy)-2-trifluoromethyl-nicotinamide The title compound was synthesized in analogy to Example 1d, using 5-bromo-N-(2-cyclopropyl-2-hydroxy-propyl)-6-(2,2,2-trifluoro-ethoxy)-2-trifluoromethyl-nicotinamide and 3-chlorophenylboronic acid as starting materials, MS (ISP) 531.0, 497.1 (M)$^+$.

Example 4

Preparation of 5-(4-chloro-phenyl)-N-((1R,2R)-2-hydroxy-cyclohexyl)-6-(2,2,2-trifluoro-ethoxy)-2-trifluoromethyl-nicotinamide a) 5-Bromo-N-((1R,2R)-2-hydroxy-cyclohexyl)-6-(2,2,2-trifluoro-ethoxy)-2-trifluoromethyl-nicotinamide The title compound was synthesized in analogy to Example 1c, using 5-bromo-6-(2,2,2-trifluoro-ethoxy)-2-trifluoromethyl-nicotinic acid and (1R,2R)-2-amino-cyclohexanol as starting materials, MS (ISP) 467.0 (M+H)$^+$.

b) 5-(4-Chloro-phenyl)-N-((1R,2R)-2-hydroxy-cyclohexyl)-6-(2,2,2-trifluoro-ethoxy)-2-trifluoromethyl-nicotinamide The title compound was synthesized in analogy to Example 1d, using 5-bromo-N-((1R,2R)-2-hydroxy-cyclohexyl)-6-(2,2,2-trifluoro-ethoxy)-2-trifluoromethyl-nicotinamide and 4-chlorophenylboronic acid as starting materials, MS (ISP) 497.2 (M)$^+$.

Example 4A

Preparation of 5-(4-chloro-phenyl)-N-((1S,2S)-2-hydroxy-cyclohexyl)-6-(2,2,2-trifluoro-ethoxy)-2-trifluoromethyl-nicotinamide a) 5-Bromo-N-((1S,2S)-2-hydroxy-cyclohexyl)-6-(2,2,2-trifluoro-ethoxy)-2-trifluoromethyl-nicotinamide The title compound was synthesized in analogy to Example 1c, using 5-bromo-6-(2,2,2-trifluoro-ethoxy)-2-trifluoromethyl-nicotinic acid and (1S,2S)-2-amino-cyclohexanol as starting materials, MS (ISP) 465.1, 467.1 (M+H)$^+$.

b) 5-(4-Chloro-phenyl)-N-((1S,2S)-2-hydroxy-cyclohexyl)-6-(2,2,2-trifluoro-ethoxy)-2-trifluoromethyl-nicotinamide The title compound was synthesized in analogy to Example 1d, using 5-bromo-N-((1S,2S)-2-hydroxy-cyclohexyl)-6-(2,2,2-trifluoro-ethoxy)-2-trifluoromethyl-nicotinamide and 4-chlorophenylboronic acid as starting materials, MS (ISP) 497.1 (M+H)$^+$.

Example 4B (Method A)

Preparation of 5-(4-chloro-phenyl)-N-((1R,2S)-2-hydroxy-cyclohexyl)-6-(2,2,2-trifluoro-ethoxy)-2-trifluoromethyl-nicotinamide a) 1,4,5,6-Tetrahydro-6-oxo-2-(trifluoromethyl)-3-pyridinecarboxylic acid ethyl ester To 3-amino-4,4,4-trifluoro-2-butenoic acid ethyl ester (529 mL, 3.47 mol) was added acryloylchloride (600 mL, 6.95 mol) dropwise over a period of 15 min. The suspension was stirred at RT for 1 h. The temperature was slowly raised with stirring to 80° C. (HCl gas evolution) and maintained at 80° C. for 5 h. Stirring continued overnight at 40° C. The mixture was cooled, diluted with toluene (2 L) and n-heptane (2 L) to precipitate the product and stirred for another 15 min at room temperature. The product was isoloated by filtration, the filter cake was washed with toluene/n-heptane (1:2; 4×100 mL) and dried in vacuo at 40° C. for 5 h. This procedure yielded the title compound (286 g, 35%) as a white solid, MS (ISP) 236.1 (M−H)$^-$. Concentration of the mother liquor and addition of toluene/n-heptane (1:10) yielded a second crop of 29.8 g.

b) 1,6-Dihydro-6-oxo-2-(trifluoromethyl)-3-pyridinecarboxylic acid ethyl ester To a suspension of 1,4,5,6-tetrahydro-6-oxo-2-(trifluoromethyl)-3-pyridinecarboxylic acid ethyl ester (136.15 g, 0.57 mol) in tetrachloromethane (450 mL) was added N-bromosuccinimide (113 g, 0.60 mol). The temperature was slowly raised with stirring to 70° C. and reflux temperature was maintained for 20 h. The mixture was cooled and extracted with water (1000 mL) and dichlormethane (1000 mL). The water phase was extracted twice more with dichloromethane (2×500 mL) and the dichloromethane phases washed with water (2×1000 mL) and dried with MgSO4. Removal of the solvents yielded the title compound (153.4 g), which was used without further purification in the next reaction.

c) 5-Bromo-1,6-dihydro-6-oxo-2-(trifluoromethyl)-3-pyridinecarboxylic acid ethyl ester To a solution of 1,6-dihydro-6-oxo-2-(trifluoromethyl)-3-pyridinecarboxylic acid ethyl ester (157.6 g, 0.60 mol) in tetrahydrofuran (1500 mL) was added with stirring N-bromosuccinimide (124.3 g, 0.66 mol). The mixture was stirred for 1 h at room temperature. Two thirds of the solvent were removed in vacuo and the remaining material was poured portionwise (15 min) with stirring into cold water (20 L). The product precipitated and the suspension was stirred for 1 h at room temperature, filtered and the filter cake was washed extensively with water (6×200 mL). The filter cake was redissolved in ethyl acetate (2000 mL), dried with MgSO$_4$ and concentrated to a volume of ~300 mL. This solution was added dropwise into n-heptane (800 mL) to precipitate the product. Filtration and washing with n-heptane/ethyl acetate (4:1, 4×50 mL) and drying (in vacuo, 40° C.) yielded the title compound (93 g) as a white solid. Concentration of the mother liquor and addition of n-heptane/ethyl acetate (3:1, 150 mL) yielded a second crop of 16.4 g.

d) 5-Bromo-6-(2,2,2-trifluoro-ethoxy)-2-trifluoromethyl-nicotinic acid ethyl ester 5-Bromo-1,6-dihydro-6-oxo-2-(trifluoromethyl)-3-pyridinecarboxylic acid ethyl ester (111 g, 0.35 mol) was dissolved in tetrahydrofuran (1600 mL). To the solution were added trifluoroethanol (38 mL, 0.53 mol), triphenylphosphine (117 g, 0.42 mol) and diisopropyl azodicarboxylate (89.4 mL, 0.42 mol) at 0° C. The mixture was stirred for 30 min at 0° C., for 1 h at room temperature and for 18 h at 50° C. The mixture was cooled, poured into n-heptane (3.8 L) and extracted with 80% methanol (2×3.8 L). The methanol phase was extracted with another 3.8 L of n-heptane, the n-heptane phases were combined and dried with MgSO$_4$. The solvent was removed in vacuo to give the title compound (121.5 g) as yellowish oil.

f) 5-Bromo-6-(2,2,2-trifluoro-ethoxy)-2-trifluoromethyl-nicotinic acid

5-Bromo-6-(2,2,2-trifluoro-ethoxy)-2-trifluoromethyl-nicotinic acid ethyl ester (244 g, 0.61 mol) was dissolved in a mixture of tetrahydrofuran (2100 mL) and water (700 mL). Lithiumhydroxid monohydrate (77 g, 1.85 mol) was added and the mixture was stirred and heated at reflux-temperature for 1.5 h. After cooling to room temperature the mixture was acidified with hydrochloric acid (2N, 750 mL). The mixture was extracted with diethylether (1×1500 mL, 1×1000 mL), and the organic phases were washed with brine (1000 mL). The organic phases were combined, dried with MgSO$_4$ and the solvent was evaporated to give the title compound (224 g) as off-white solid; MS (ISP) 365.9, 367.9 (M−H).

g) 5-Bromo-N-((1RS,2SR)-2-hydroxy-cyclohexyl)-6-(2,2,2-trifluoro-ethoxy)-2-trifluoromethyl-nicotinamide To a solution of 5-bromo-6-(2,2,2-trifluoro-ethoxy)-2-trifluoromethyl-nicotinic acid (94.0 g, 0.255 mol) in DMF (900 mL) was added with stirring TBTU (90.2 g, 0.28 mol), N,N-diisopropyl ethylamine (219 mL) and cis-2-aminocyclohexanol hydrochloride (42.6 g, 0.28 mol). The temperature rose to 35° C. After stirring was for 3 h the mixture was concentrated in high vacuo at 45° C. The residue was extracted with cold 1N—NaOH (2 L) and ethylacetate (1×2.5 L, 1×1.5 L).

Organic phases were washed with water (2×1.5 L). The organic phases were combined, dried with MgSO4 and concentrated in vacuo to ~800-900ml volume. The product precipitated and the mixture was stirred at 0° C. for about 30 min. Filtration, washing with ethyl acetate/n-heptane 1:1 (4×50 mL) and drying in vacuo at 40° C. for 18 h yielded the title compound (75.8 g as a white solid); MS (ISP) 465.0, 467.0 (M+H)+.

h) 5-Bromo-N-((1R,2S)-2-hydroxy-cyclohexyl)-6-(2,2,2-trifluoro-ethoxy)-2-trifluoromethyl-nicotinamide 5-Bromo-N-((1RS,2SR)-2-hydroxy-cyclohexyl)-6-(2,2,2-trifluoro-ethoxy)-2-trifluoromethyl-nicotinamide (103 g) was subjected to chiral chromatography on ChiralPak AD with 5% isopropanol/n-heptane as eluent. The product eluted as second peak to give after evaporation of the solvent the title compound (43.3 g) as a white solid, MS (ISP) 465.0, 467.0 (M+H)+; $[\alpha]_D^{20}$+19.1°.

i) 5-(4-Chloro-phenyl)-N-((1R,2S)-2-hydroxy-cyclohexyl)-6-(2,2,2-trifluoro-ethoxy)-2-trifluoromethyl-nicotinamide The title compound was synthesized in analogy to Example 1d, using 5-bromo-N-((1R,2S)-2-hydroxy-cyclohexyl)-6-(2,2,2-trifluoro-ethoxy)-2-trifluoromethyl-nicotinamide and 4-chlorophenylboronic acid as starting materials, MS (ISP) 497.1 (M+H)+; $[\alpha]_D^{20}$=+22.2°.

Example 4B (Method B)

Preparation of 5-(4-chloro-phenyl)-N-((1R,2S)-2-hydroxy-cyclohexyl)-6-(2,2,2-trifluoro-ethoxy)-2-trifluoromethyl-nicotinamide a) 5-(4-Chloro-phenyl)-6-(2,2,2-trifluoro-ethoxy)-2-trifluoromethyl-nicotinic acid 5-Bromo-6-(2,2,2-trifluoro-ethoxy)-2-trifluoromethyl-nicotinic acid ethyl ester (2 g, 5.05 mmol) was dissolved in ethanol (30 ml). To this solution was added with stirring [1,1'-bis(diphenylphosphino)ferrocene]dichloropalladium (II) CH$_2$Cl$_2$ (41.2 mg, 0.05 mmol), 4-chlorophenylboronic acid (828.8 mg, 5.3 mmol), water (4.8 ml) and lithium hydroxide (246.7 mg, 10.1 mmol). This mixture was heated to 70° C. for 2.5 h and cooled to room temperature. Water (12 mL) and lithium hydroxide (370.0 mg, 15.1 mmol) was added and stirred at 70° C. for 0.5 h. The reaction mixture was cooled to room temperature, treated with water (40 ml) and toluene (40 ml) and extracted. The phases were separated, the organic phase extracted with water (30 ml). The combined water phase was acidified with HCl 2N and extracted with ethylacetate. Organic phases were pooled, dried with Na2SO4 and the volatiles removed in vacuo. The residue was dissolved in ethanol (6 ml) and treated with water (12 ml) to give after crystallization the title compound (1.82 g) as light brown crystals; MS (ISN) 398.0 (M−H)−.

b) 5-(4-Chloro-phenyl)-N-((1R,2S)-2-hydroxy-cyclohexyl)-6-(2,2,2-trifluoro-ethoxy)-2-trifluoromethyl-nicotinamide 5-(4-Chloro-phenyl)-6-(2,2,2-trifluoro-ethoxy)-2-trifluoromethyl-nicotinic acid (1.5 g, 3.75 mmol) was dissolved in a mixture of THF (15 ml) and DMF (11.4 µl). To this solution was added with stirring oxalyl chloride (0.52 ml, 6.0 mmol), whereby at room temperature after 1 h the corresponding acid chloride was formed. (1R,2S)-2-Hydroxy-cyclohexyl-ammonium; chloride (608.9 mg, 4.02 mmol) was dissolved in a mixture of THF (6 ml) and water (6 ml). This solution was treated with NaOH 32% (1.74 ml, 18.8 mmol) and stirred at room temperature for 1 h. To this solution was added the above produced acid chloride and stirred at room temperature for 1 h. The reaction mixture was poured onto water (120 ml) and the formed precipitation filtered. The brown crystals were dissolved under reflux in ethanol (12 ml), cooled to room temperature, treated with water (10 ml) yielding after filtration and drying the title compound (1.62 g) as light grey crystals; MS (ISP) 497.1 (M+H)+.

c) N-((1R,2R)-2-Hydroxy-cyclohexyl)-acetamide (1R,2R)-2-Amino-cyclohexanole hydrochloric acid (25.0 g, 164.9 mmol) was dissolved in acetone (160 ml). To this solution was added at 0° C. with stirring aqueous sodium carbonate (163.7 ml, 169.8 mmol) and within 10 minutes acetic anhydride. The reaction mixture was stirred at room temperature for 2 h and the solvent evaporated. The residue was treated at room temperature with ethanol (200 ml), stirred for 5 min. After filtration the solvent was evaporated and treated with dichloromethane (300 ml), stirred at reflux for 2 h and again filtered. The solvent of the filtrate was evaporated to yield the title compound (25.9 g) as white solid; MS (ISP) 158.2 (M+H)+.

d) (3aR,7aS)-2-Methyl-3a,4,5,6,7,7a-hexahydro-benzooxazol-3-ium; chloride

N-((1R,2R)-2-Hydroxy-cyclohexyl)-acetamide (26.0 g, 163.7 mmol) was dissolved in dichloromethane (200 ml) and treated at 0° C. within 10 min with thionyl chloride (50.4 ml, 687.5 mmol). The reaction was warmed to room temperature within 1 h (orange precipitation) and stirred at room temperature for 16 h. The solvent was evaporated to yielding the title compound in quantitative yield (ca. 90% purity; MS (ISP) 140.3 (M+H)+.

e) (1R,2S)-2-Hydroxy-cyclohexyl-ammonium; chloride (3aR,7aS)-2-Methyl-3a,4,5,6,7,7a-hexahydro-benzooxazol-3-ium; chloride (33 g, 159.7 mmol) were dissolved in a mixture of water (330 ml) and HCl (25%, 229 ml). The solution was heated to reflux for 1 h, cooled to room temperature, filtrated over speedex and the solvent evaporated. The residue was dissolved under reflux in ethanol (150 ml), filtered and the filtrate treated with TBME (300 ml). The formed crystals were filtered and dried to yield the title compound (14.2 g) as white crystals; MS (ISP) 116.1 (M+H)+.

Example 4C

Preparation of 5-(4-chloro-phenyl)-N-((1S,2R)-2-hydroxy-cyclohexyl)-6-(2,2,2-trifluoro-ethoxy)-2-trifluoromethyl-nicotinamide h) 5-Bromo-N-((1S,2R)-2-hydroxy-cyclohexyl)-6-(2,2,2-trifluoro-ethoxy)-2-trifluoromethyl-nicotinamide 5-Bromo-N-((1RS,2SR)-2-hydroxy-cyclohexyl)-6-(2,2,2-trifluoro-ethoxy)-2-trifluoromethyl-nicotinamide (103 g) was subjected to chiral chromatography on ChiralPak AD with 5% isopropanol/n-heptane as eluent. The product eluted as first peak to give after evaporation of the solvent the title compound (42.4 g) as a white solid, MS (ISP) 465.0, 467.0 (M+H)$^+$; $[\alpha]_D^{20}$=−19.8°.

i) 5-(4-Chloro-phenyl)-N-((1S,2R)-2-hydroxy-cyclohexyl)-6-(2,2,2-trifluoro-ethoxy)-2-trifluoromethyl-nicotinamide The title compound was synthesized in analogy to Example 1d, using 5-bromo-N-((1S,2R)-2-hydroxy-cyclohexyl)-6-(2,2,2-trifluoro-ethoxy)-2-trifluoromethyl-nicotinamide and 4-chlorophenylboronic acid as starting materials, MS (ISP) 497.1 (M+H)$^+$; $[\alpha]_D^{20}$=−20.0°.

Example 5

Preparation of N-(1-hydroxymethyl-3-methyl-butyl)-5-(4-methanesulfonylamino-phenyl)-6-(pyridin-2-ylmethoxy)-2-trifluoromethyl-nicotinamide a) 5-Bromo-6-(pyridin-2-ylmethoxy)-2-trifluoromethyl-nicotinic acid ethyl ester The title compound was synthesized in analogy to Example 1a, using 5-bromo-1,6-dihydro-6-oxo-2-(trifluoromethyl)-3-pyridinecarboxylic acid ethyl ester (CAS Registry No. 862111-61-3) and 2-(hydroxymethyl)-pyridine as starting materials, MS (ISP) 407.1 (M+H)$^+$.

b) 5-Bromo-6-(pyridin-2-ylmethoxy)-2-trifluoromethyl-nicotinic acid

The title compound was synthesized in analogy to Example 1b, using 5-bromo-6-(pyridin-2-ylmethoxy)-2-trifluoromethyl-nicotinic acid ethyl ester as starting material, MS (ISP) 375.0 (M−H)$^+$.

c) 5-Bromo-N-(1-hydroxymethyl-3-methyl-butyl)-6-(pyridin-2-ylmethoxy)-2-trifluoromethyl-nicotinamide The title compound was synthesized in analogy to Example 1c, using 5-bromo-6-(pyridin-2-ylmethoxy)-2-trifluoromethyl-nicotinic acid and rac-leucinol as starting materials, MS (ISP) 476.1 (M+H)$^+$.

d) N-(1-Hydroxymethyl-3-methyl-butyl)-5-(4-methanesulfonylamino-phenyl)-6-(pyridin-2-ylmethoxy)-2-trifluoromethyl-nicotinamide The title compound was synthesized in analogy to Example 1d, using 5-bromo-N-(1-hydroxymethyl-3-methyl-butyl)-6-(pyridin-2-ylmethoxy)-2-trifluoromethyl-nicotinamide and 4-methanesulfonylaminophenylboronic acid as starting materials, MS (ISP) 567.2 (M)$^+$.

Example 6

Preparation of N-((1R,2R)-2-hydroxy-cyclohexyl)-5-(4-methanesulfonylamino-phenyl)-6-(2,2,2-trifluoro-ethoxy)-2-trifluoromethyl-nicotinamide The title compound was synthesized in analogy to Example 1d, using 5-bromo-N-((1R,2R)-2-hydroxy-cyclohexyl)-6-(2,2,2-trifluoro-ethoxy)-2-trifluoromethyl-nicotinamide and 4-methanesulfonylaminophenylboronic acid as starting materials, MS (ISP) 556.1 (M+H)$^+$.

Example 7

Preparation of 5-(3,4-dichloro-phenyl)-N-((1R,2R)-2-hydroxy-cyclohexyl)-6-(pyridin-2-ylmethoxy)-2-trifluoromethyl-nicotinamide a) 5-Bromo-N-((1R,2R)-2-hydroxy-cyclohexyl)-6-(pyridin-2-ylmethoxy)-2-trifluoromethyl-nicotinamide The title compound was synthesized in analogy to Example 1c, using 5-bromo-6-(pyridin-2-ylmethoxy)-2-trifluoromethyl-nicotinic acid and (1R,2R)-2-amino-cyclohexanol as starting materials, MS (ISP) 476.1 (M+H)$^+$.

b) 5-(3,4-Dichloro-phenyl)-N-((1R,2R)-2-hydroxy-cyclohexyl)-6-(pyridin-2-ylmethoxy)-2-trifluoromethyl-nicotinamide The title compound was synthesized in analogy to Example 1d, using 5-bromo-N-((1R,2R)-2-hydroxy-cyclohexyl)-6-(pyridin-2-ylmethoxy)-2-trifluoromethyl-nicotinamide and 3,4-dichlorophenylboronic acid as starting materials, MS (ISP) 540.1 (M+H)$^+$.

Example 8

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magesium stearate and compressed to yield kernels of 120 or 350 mg respectively. The kernels are lacquered with an aq. solution/suspension of the above mentioned film coat.

Example 9

Capsules containing the following ingredients can be manufactured in a conventional manner:

| Ingredients | Per capsule |
| --- | --- |
| Compound of formula (I) | 25.0 mg |
| Lactose | 150.0 mg |

-continued

| Ingredients | Per capsule |
|---|---|
| Maize starch | 20.0 mg |
| Talc | 5.0 mg |

The components are sieved and mixed and filled into capsules of size 2.

Example 10

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

Unless stated to the contrary, all compounds in the examples were prepared and characterized as described. All ranges recited herein encompass all combinations and sub-combinations included within that range limit. All patents and publications cited herein are hereby incorporated by reference in their entirety.

The invention claimed is:
1. A compound of formula I:

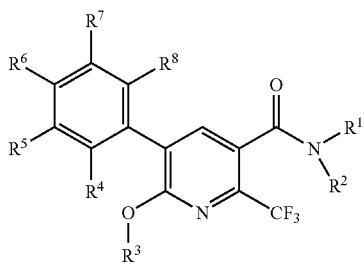

or a pharmaceutically acceptable salt thereof, wherein:
$R^1$ is selected from the group consisting of:
 (1) lower hydroxyalkyl,
 (2) cycloalkyl which is unsubstituted or substituted by hydroxy or lower hydroxyalkyl, and
 (3) —$CH_2$—$CR^9R^{10}$-cycloalkyl, wherein $R^9$ is hydrogen or lower alkyl, and $R^{10}$ is hydrogen or hydroxy;
$R^2$ is hydrogen;
$R^3$ is selected from the group consisting of:
 (1) lower alkoxyalkyl,
 (2) lower halogenalkyl, and
 (3) lower heteroarylalkyl, wherein the heteroaryl group is unsubstituted or substituted once or twice by lower alkyl;
$R^4$ and $R^8$ are hydrogen; and $R^5$, $R^6$ and $R^7$ independently from each other are selected from the group consisting of:
 (1) hydrogen,
 (2) lower alkyl,
 (3) halogen,
 (4) lower halogenalkyl,
 (5) lower halogenalkoxy,
 (6) lower alkylsulfonylamino, and
 (7) cyano.

2. A compound of formula I according to claim 1, wherein $R^3$ is lower halogenalkyl or lower heteroarylalkyl, wherein the heteroaryl group is unsubstituted or mono- or di-substituted by lower alkyl.

3. A compound of formula I according to claim 1, wherein $R^3$ is lower halogenalkyl.

4. A compound of formula I according to claim 1, wherein $R^3$ is lower heteroarylalkyl, wherein the heteroaryl group is unsubstituted or mono- or di-substituted by lower alkyl.

5. A compound of formula I according to claim 1, wherein $R^1$ is cycloalkyl substituted by hydroxy.

6. A compound of formula I according to claim 1, wherein $R^1$ is —$CH_2$—$CR^9R^{10}$-cycloalkyl and wherein $R^9$ is methyl and $R^{10}$ is hydroxy.

7. A compound of formula I according to claim 1, wherein $R^1$ is lower hydroxyalkyl.

8. A compound of formula I according claim 1, wherein at least one of $R^5$, $R^6$ and $R^7$ is selected from the group consisting of lower alkyl, halogen, lower halogenalkyl, lower halogenalkoxy, lower alkylsulfonylamino and cyano.

9. A compound of formula I according to claim 1, wherein at least one of $R^5$, $R^6$ and $R^7$ is selected from the group consisting of halogen and lower alkylsulfonylamino.

10. A compound of formula I according to claim 1, wherein $R^6$ is halogen or lower alkylsulfonylamino and $R^5$ and $R^7$ are hydrogen.

11. A compound of formula I according to claim 1, wherein $R^5$ and $R^6$ are halogen and $R^7$ is hydrogen.

12. A compound of claim 1 selected from the group consisting of:
 5-(4-chloro-phenyl)-N-(2-cyclopropyl-2-hydroxy-propyl)-6-(2,2,2-trifluoro-ethoxy)-2-trifluoromethyl-nicotinamide,
 N-(2-cyclopropyl-2-hydroxy-propyl)-5-(3,4-dichloro-phenyl)-6-(2,2,2-trifluoro-ethoxy)-2-trifluoromethyl-nicotinamide,
 N—((R)-2-cyclopropyl-2-hydroxy-propyl)-5-(3,4-dichloro-phenyl)-6-(2,2,2-trifluoro-ethoxy)-2-trifluoromethyl-nicotinamide
 N—((S)-2-cyclopropyl-2-hydroxy-propyl)-5-(3,4-dichloro-phenyl)-6-(2,2,2-trifluoro-ethoxy)-2-trifluoromethyl-nicotinamide
 5-(3-chloro-phenyl)-N-(2-cyclopropyl-2-hydroxy-propyl)-6-(2,2,2-trifluoro-ethoxy)-2-trifluoromethyl-nicotinamide,
 5-(4-chloro-phenyl)-N-((1R,2R)-2-hydroxy-cyclohexyl)-6-(2,2,2-trifluoro-ethoxy)-2-trifluoromethyl-nicotinamide,
 5-(4-chloro-phenyl)-N-((1R,2S)-2-hydroxy-cyclohexyl)-6-(2,2,2-trifluoro-ethoxy)-2-trifluoromethyl-nicotinamide,
 5-(4-chloro-phenyl)-N-((1S,2R)-2-hydroxy-cyclohexyl)-6-(2,2,2-trifluoro-ethoxy)-2-trifluoromethyl-nicotinamide,
 5-(4-chloro-phenyl)-N-((1S,2S)-2-hydroxy-cyclohexyl)-6-(2,2,2-trifluoro-ethoxy)-2-trifluoromethyl-nicotinamide, N-(1-hydroxymethyl-3-methyl-butyl)-5-(4-methane-sulfonylamino-phenyl)-6-(pyridin-2-ylmethoxy)-2-trifluoromethyl-nicotinamide, N-((1R,2R)-2-hydroxy-cyclohexyl)-5-(4-methanesulfonylamino-phenyl)-6-(2,2,2-trifluoro-ethoxy)-2-trifluoromethyl-nicotinamide, 5-(3,4-dichloro-phenyl)-N-((1R,2R)-2-hydroxy-cyclohexyl)-6-(pyridin-2-ylmethoxy)-2-trifluoromethyl-nicotinamide, and a pharmaceutically acceptable salt thereof.

13. A compound of claim 1 which is 5-(4-Chloro-phenyl)-N-((1R,2S)-2-hydroxy-cyclohexyl)-6-(2,2,2-trifluoro-ethoxy)-2-trifluoromethyl-nicotinamide.

14. A compound of claim 1 which is 5-(4-chloro-phenyl)-N-(2-cyclopropyl-2-hydroxy-propyl)-6-(2,2,2-trifluoro-ethoxy)-2-trifluoromethyl-nicotinamide.

15. A compound of claim 1 which is N-(2-cyclopropyl-2-hydroxy-propyl)-5-(3,4-dichloro-phenyl)-6-(2,2,2-trifluoro-ethoxy)-2-trifluoromethyl-nicotinamide.

16. A compound of claim 1 which is N—((R)-2-cyclopropyl-2-hydroxy-propyl)-5-(3,4-dichloro-phenyl)-6-(2,2,2-trifluoro-ethoxy)-2-trifluoromethyl-nicotinamide.

17. A compound of claim 1 which is N—((S)-2-cyclopropyl-2-hydroxy-propyl)-5-(3,4-dichloro-phenyl)-6-(2,2,2-trifluoro-ethoxy)-2-trifluoromethyl-nicotinamide.

18. A compound of claim 1 which is 5-(3-chloro-phenyl)-N-(2-cyclopropyl-2-hydroxy-propyl)-6-(2,2,2-trifluoro-ethoxy)-2-trifluoromethyl-nicotinamide.

19. A compound of claim 1 which is 5-(4-chloro-phenyl)-N-((1R,2R)-2-hydroxy-cyclohexyl)-6-(2,2,2-trifluoro-ethoxy)-2-trifluoromethyl-nicotinamide.

20. A compound of claim 1 which is 5-(4-chloro-phenyl)-N-((1S,2R)-2-hydroxy-cyclohexyl)-6-(2,2,2-trifluoro-ethoxy)-2-trifluoromethyl-nicotinamide.

21. A compound of claim 1 which is 5-(4-chloro-phenyl)-N-((1S,2S)-2-hydroxy-cyclohexyl)-6-(2,2,2-trifluoro-ethoxy)-2-trifluoromethyl-nicotinamide.

22. A compound of claim 1 which is N-(1-hydroxymethyl-3-methyl-butyl)-5-(4-methanesulfonylamino-phenyl)-6-(pyridin-2-ylmethoxy)-2-trifluoromethyl-nicotinamide.

23. A compound of claim 1 which is N-((1R,2R)-2-hydroxy-cyclohexyl)-5-(4-methanesulfonylamino-phenyl)-6-(2,2,2-trifluoro-ethoxy)-2-trifluoromethyl-nicotinamide.

24. A compound of claim 1 which is 5-(3,4-dichloro-phenyl)-N-((1R,2R)-2-hydroxy-cyclohexyl)-6-(pyridin-2-yl-methoxy)-2-trifluoromethyl-nicotinamide.

25. A pharmaceutical composition comprising a therapeutically effective amount of a compound of formula I according to claim 1 and a pharmaceutically acceptable carrier.

26. A process for the manufacture of a compound of formula I according to claims 1, which process comprises:

a) coupling a compound of formula:

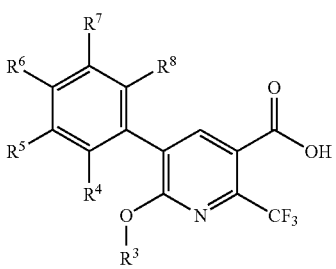

II wherein $R^3$ to $R^8$ are as defined in claim 1, with an amine of the formula:

H—NR¹R²     III wherein $R^1$ and $R^2$ are as defined in claim 1, with the help of an coupling agent under basic conditions, and optionally converting the resulting compound of formula I into a pharmaceutically acceptable salt thereof; or, alternatively, b) coupling a compound of formula:

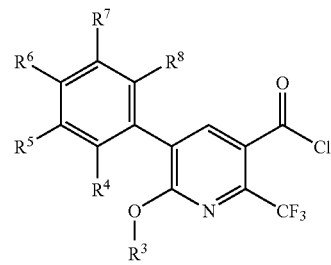

IIa wherein $R^3$ to $R^8$ are as defined in claim 1, with an amine of the formula:

H—NR¹R²     III wherein $R^1$ and $R^2$ are as defined in claim 1, and optionally converting the resulting compound of formula I into a pharmaceutically acceptable salt thereof; or, alternatively, c) coupling a compound of formula:

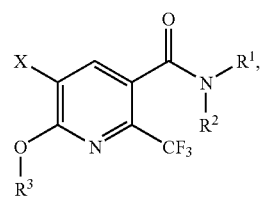

IV wherein X is halogen and $R^1$, $R^2$ and $R^3$ are as defined in claim 1, with an aryl metal species of the formula:

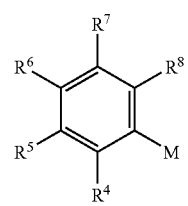

V wherein $R^4$ to $R^8$ are as defined in claim 1 and M means boronic acid or a boronic acid ester, in the presence of a Pd catalyst under basic conditions, and optionally converting the resulting compound of formula I into a pharmaceutically acceptable salt thereof.

* * * * *